(12) United States Patent
Saenz Villalobos et al.

(10) Patent No.: US 12,558,101 B2
(45) Date of Patent: *Feb. 24, 2026

(54) HEMOSTASIS CLIP

(71) Applicant: BOSTON SCIENTIFIC SCIMED, INC., Maple Grove, MN (US)

(72) Inventors: Gonzalo Jose Saenz Villalobos, Heredia (CR); Kevin Mcevilly, Galway (IE); Alejandro Brenes Acosta, San Jose (CR); Rafael Berenzon, La Union (CR); Viviana Artavia Salas, Heredia (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 56 days.

This patent is subject to a terminal disclaimer.

(21) Appl. No.: 18/677,410

(22) Filed: May 29, 2024

(65) Prior Publication Data

US 2024/0307068 A1     Sep. 19, 2024

Related U.S. Application Data

(63) Continuation of application No. 17/304,525, filed on Jun. 22, 2021, now Pat. No. 12,023,038, which is a
(Continued)

(51) Int. Cl.
*A61B 17/122*          (2006.01)
*A61B 17/08*           (2006.01)
(Continued)

(52) U.S. Cl.
CPC .......... *A61B 17/122* (2013.01); *A61B 17/083* (2013.01); *A61B 17/1227* (2013.01); (Continued)

(58) Field of Classification Search
CPC ..... A61B 17/083; A61B 17/10; A61B 17/122; A61B 17/1227; A61B 17/128; (Continued)

(56) References Cited

U.S. PATENT DOCUMENTS 7,452,327 B2 * 11/2008 Durgin ................. A61B 17/122
606/139
7,494,461 B2 * 2/2009 Wells ................. A61B 17/1285
606/151
(Continued)

*Primary Examiner* — Ryan J. Severson
(74) *Attorney, Agent, or Firm* — Fay Kaplun & Marcin, LLP

(57) ABSTRACT

A device for treating tissue includes a capsule defining a channel extending therethrough and clip arms. Each of the arms includes a proximal part releasably coupled to a distal part, a proximal portion of the distal part configured to be received within the channel of the capsule so that the arms move proximally and distally relative to the capsule between a tissue receiving configuration, in which distal ends of the arms are separated from one another, and a tissue clipping configuration, in which distal ends of the arms are moved toward one another. The proximal portion of each of the arms is configured to release from the corresponding distal part to lock the distal part of each of the arms over a portion of target tissue to be clipped while the proximal parts of the arms are removed from the body.

16 Claims, 3 Drawing Sheets

Related U.S. Application Data continuation of application No. 16/251,399, filed on Jan. 18, 2019, now Pat. No. 11,071,552.

(60) Provisional application No. 62/623,282, filed on Jan. 29, 2018.

(51) Int. Cl.
| | | |
|---|---|---|
| *A61B 17/128* | (2006.01) | |
| *A61B 17/10* | (2006.01) | |
| *A61B 17/12* | (2006.01) | |

(52) U.S. Cl.
CPC ........ *A61B 17/128* (2013.01); *A61B 17/1285* (2013.01); *A61B 17/10* (2013.01); *A61B 2017/12004* (2013.01)

(58) Field of Classification Search
CPC ...... A61B 17/1285; A61B 2017/00818; A61B 2017/12004
See application file for complete search history.

(56)                References Cited

U.S. PATENT DOCUMENTS

| | | | | |
|---|---|---|---|---|
| 8,663,247 | B2 * | 3/2014 | Menn ................... | A61B 17/122 606/142 |
| 8,979,891 | B2 * | 3/2015 | McLawhorn .......... | A61B 17/08 606/142 |
| 9,005,219 | B2 * | 4/2015 | Cohen ................ | A61B 17/1285 606/151 |
| 9,138,234 | B2 * | 9/2015 | Li ......................... | A61B 17/122 |
| 9,585,674 | B2 * | 3/2017 | Terada ................... | B21D 53/36 |
| 11,071,552 | B2 * | 7/2021 | Saenz Villalobos ........................ A61B 17/128 |
| 12,023,038 | B2 * | 7/2024 | Saenz Villalobos ........................ A61B 17/1227 |
| 2005/0070758 | A1 * | 3/2005 | Wells ................. | A61B 17/1285 600/104 |
| 2005/0080440 | A1 * | 4/2005 | Durgin ................. | A61B 17/122 606/151 |
| 2010/0152753 | A1 * | 6/2010 | Menn ................... | A61B 17/083 606/158 |
| 2011/0046651 | A1 * | 2/2011 | Cohen ................ | A61B 17/1285 606/157 |
| 2012/0165863 | A1 * | 6/2012 | McLawhorn ........ | A61B 17/122 606/207 |
| 2013/0072947 | A1 * | 3/2013 | Terada ................... | B21D 53/36 72/332 |
| 2013/0123818 | A1 * | 5/2013 | Li ......................... | A61B 17/122 606/157 |
| 2015/0190136 | A1 * | 7/2015 | Cohen ................ | A61B 17/1227 606/143 |
| 2019/0231353 | A1 * | 8/2019 | Saenz Villalobos ........................ A61B 17/1285 |
| 2021/0307755 | A1 * | 10/2021 | Saenz Villalobos ........................ A61B 17/122 |

* cited by examiner

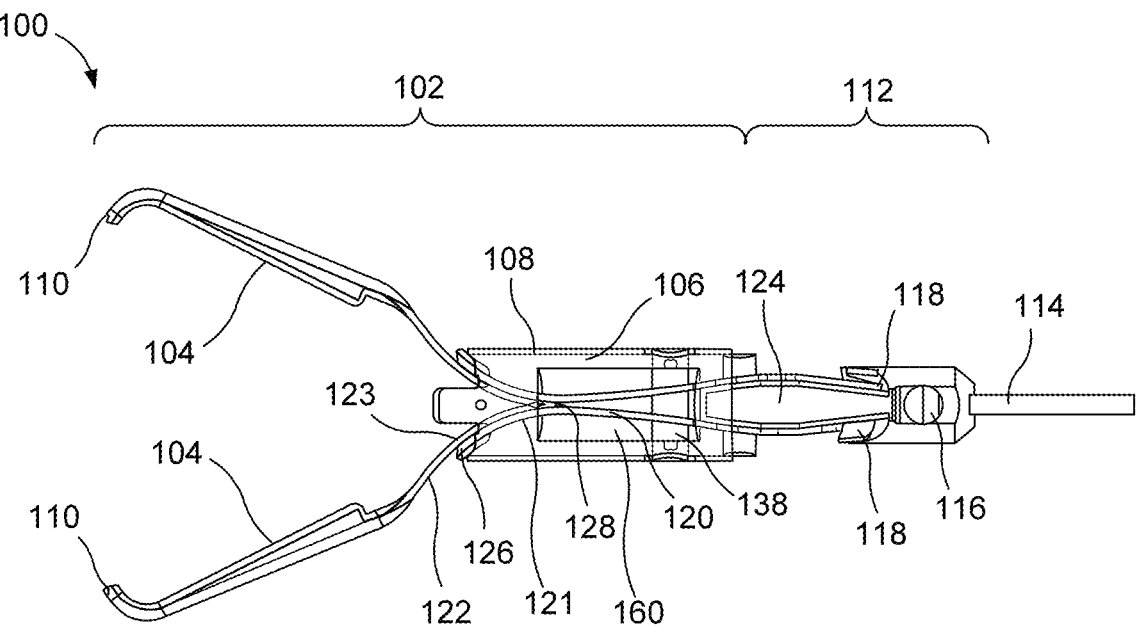
F I G. 1
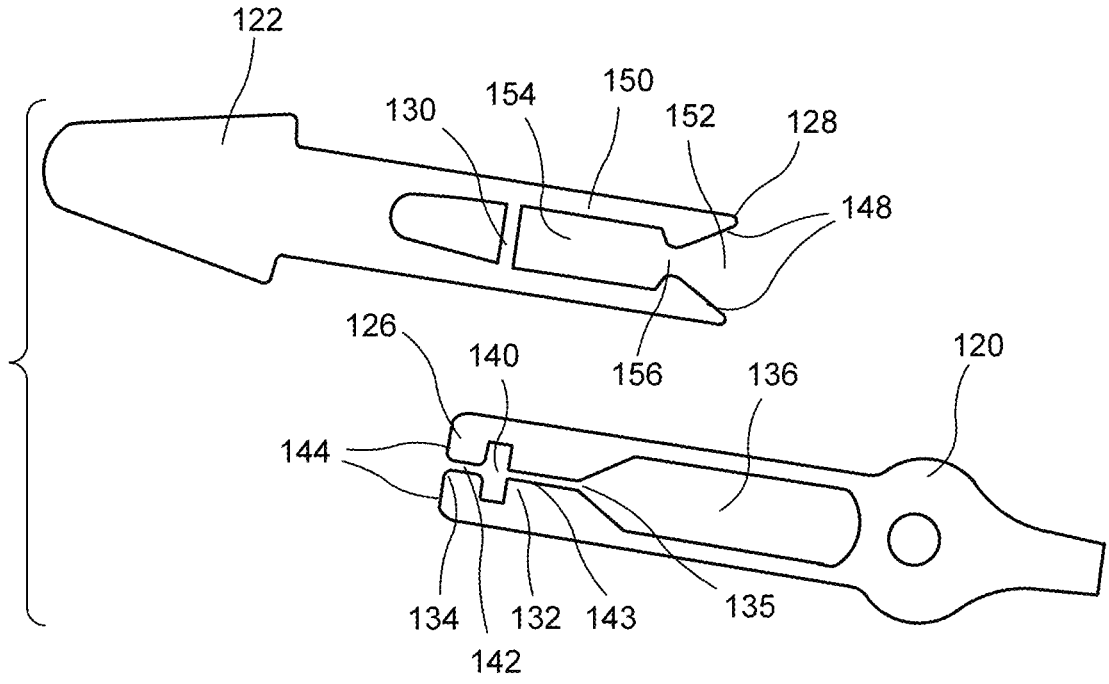
F I G. 2

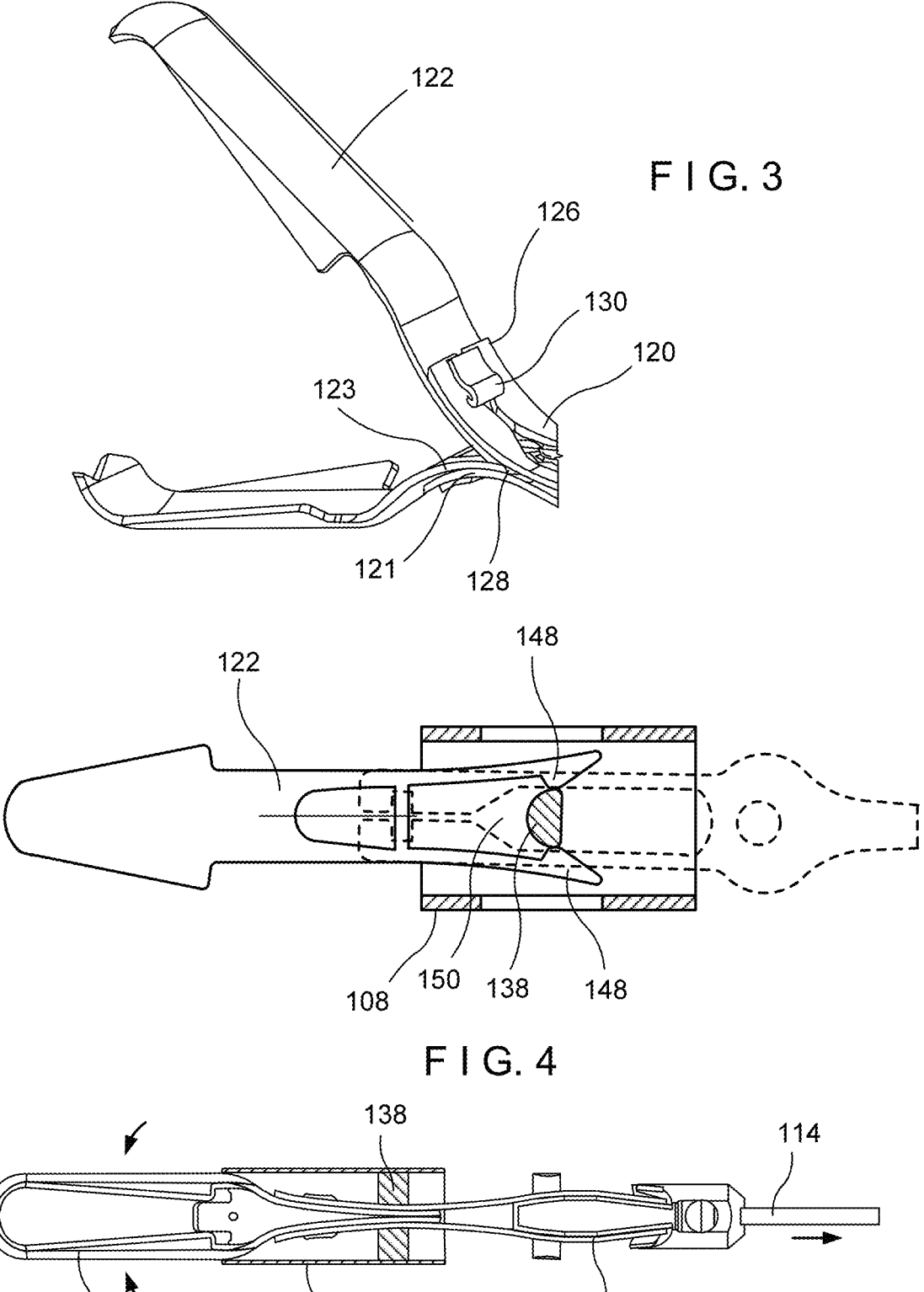
F I G. 3
F I G. 4
F I G. 5

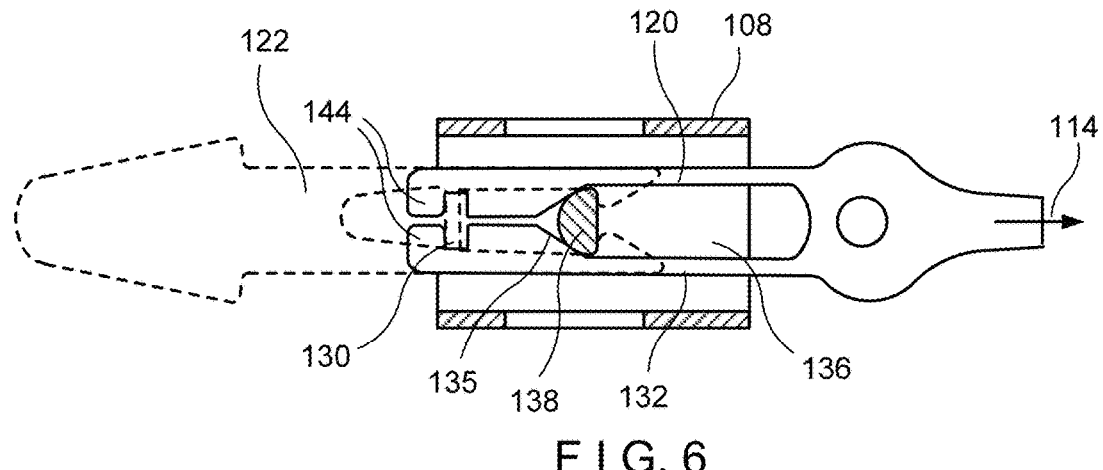
F I G. 6
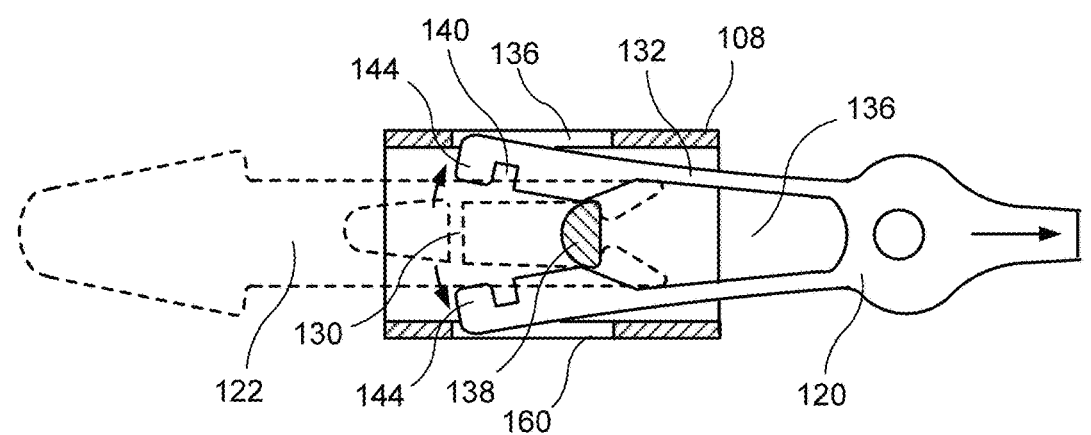
F I G. 7
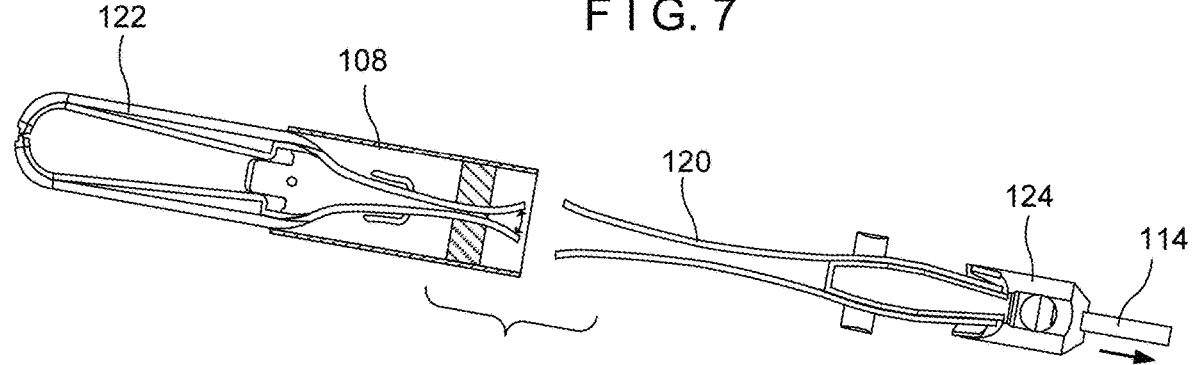
F I G. 8

HEMOSTASIS CLIP

PRIORITY CLAIM

The present application is a Continuation of U.S. patent application Ser. No. 17/304,525 filed Jun. 22, 2021, now U.S. Pat. No. 12,023,038; which is a Continuation of U.S. patent application Ser. No. 16/251,399 filed Jan. 18, 2019, now U.S. Pat. No. 11,071,552; which claims priority to U.S. Provisional Patent Application Ser. No. 62/623,282 filed Jan. 29, 2018. The disclosures of the above application(s)/ patent(s) are incorporated herewith by reference.

FIELD OF THE DISCLOSURE

The present disclosure relates to compression clips, and more specifically, to compression clips delivered to a target site through an endoscope to cause hemostasis of blood vessels located along the gastrointestinal tract.

BACKGROUND

Pathologies of the gastrointestinal (GI) system, including the esophageal tract, stomach, biliary tree, duodenal tract, colonic tract and associated anatomies are often treated through endoscopic procedures, many of which require active and/or prophylactic hemostasis to control internal bleeding. Catheter-based minimally invasive devices for deploying hemostatic clips via endoscopes are often used to stop internal bleeding by clamping together the edges of wounds or incisions. Hemostatic clips grab tissue surrounding a wound and hold edges of the wound together to allow natural healing processes to close the wound. Specialized endoscopic clipping devices are used to deliver the clips to desired locations within the body and to position and deploy the clips in the desired locations within the body after which the clip delivery device is withdrawn, leaving the clip within the body. Typical procedures involve more than one clip to close larger injured areas or to address multiple sites of bleeding.

Current hemostatic clips typically involve a capsule long enough to contain a portion of the length of tissue gripping arms after deployment and a deployment mechanism that pulls and pushes the arms in and out of the capsule to open and close the arms. For a variety of reasons, current clips are often large making it difficult to navigate in tight areas and to place additional clips near an injured area where one or more clips have already been deployed.

SUMMARY

The present disclosure relates to a device for treating tissue. The device includes a capsule defining a channel extending therethrough and first and second clip arms each including a proximal part releasably coupled to a distal part, at least a proximal portion of the distal part of each of the first and second clip arms configured to be slidably received within a channel of the capsule so that the first and second clip arms move proximally and distally relative to the capsule between a tissue receiving configuration, in which distal ends of the first and second clip arms are separated from one another, and a tissue clipping configuration, in which distal ends of the first and second clip arms are moved toward one another, the proximal portion of each of the first and second clip arms being configured to release from the corresponding distal part to lock the distal part of each of the first and second clip arms over a portion of target tissue to be clipped while the proximal parts of the first and second clip arms are removed from the body.

In an embodiment, the capsule includes a cam extending into the channel, the cam being sized and shaped to extend through a first longitudinal slot of the proximal part to releasably couple the clip arms to the capsule, the first longitudinal slot extending from a distal opening at a distal end of the proximal part to a slot proximal end, the first longitudinal slot defining a first pair of opposing portions biased toward one another.

In an embodiment, the first longitudinal slot includes a proximal portion configured to receive the cam when the arms are in the tissue receiving configuration and a distal portion extending between the distal opening and the proximal portion, the distal portion having a cross-sectional area smaller than a cross-sectional area of the cam.

In an embodiment, the coupling mechanism includes a hook extending distally from an outer surface of the distal portion, the hook being removably received within a hook receiving space of the proximal part, the hook receiving space being positioned distally of the proximal portion of the first longitudinal slot.

In an embodiment, the first longitudinal slot proximal portion includes a distal tapered portion that tapers distally to the distal portion so that when the cam abuts the distal tapered portion, a proximal force on the proximal part spreads the first opposed portions apart permitting the cam and the hook to pass distally out of the first longitudinal slot disengaging the proximal part from the capsule and the distal part.

In an embodiment, the distal part includes a second longitudinal slot extending from a proximal opening at a proximal end of the distal part to a slot distal end, the second longitudinal slot defining a pair of opposed portions biased toward one another, the opposed portions being spreadable to permit the cam to pass distally into the second longitudinal slot locking the distal part to the capsule in the tissue clipping configuration.

In an embodiment, the second longitudinal slot includes a proximal neck portion and a distal portion, the neck portion having a cross-sectional area smaller than a cross-sectional area of the cam.

In an embodiment, the proximal opening tapers from the proximal end to the neck portion to guide the cam into the second longitudinal slot.

In an embodiment, the capsule includes a pair of windows providing space required for the first opposed portions to move around the cam.

The present disclosure also relates to a system for clipping tissue. The system includes an insertion member including a lumen extending therethrough, a control member extending through the insertion member lumen, a distal end of the control member coupling to a connection member and a proximal end of the control member being coupled to an actuator that remains accessible to a user so that actuation of the actuator moves the control member and the connection member distally and proximally relative to the insertion member and a clip coupled to the connection member, the clip including a capsule including a proximal end releasably coupled to a distal end of the insertion member, the capsule defining a channel extending therethrough, and first and second clip arms each including a proximal part releasably coupled to a distal part, at least a proximal portion of the distal part of each of the first and second clip arms configured to be slidably received within a channel of the capsule so that, as actuation of the actuator moves the control member and the connection member to move proximally and distally relative to the insertion member, the first and second clip arms move proximally and distally relative to the capsule between a tissue receiving configuration, in which distal ends of the first and second clip arms are separated from one another, and a tissue clipping configuration, in which distal ends of the first and second clip arms are moved toward one another, the proximal portion of each of the first and second clip arms being configured to release from the corresponding distal part to lock the distal part of each of the first and second clip arms over a portion of target tissue to be clipped while the proximal parts of the first and second clip arms are removed from the body.

In an embodiment, the capsule includes a cam extending into the channel, the cam being sized and shaped to extend through a first longitudinal slot of the proximal part to releasably couple the clip arms to the capsule, the first longitudinal slot extending from a distal opening at a distal end of the proximal part to a slot proximal end, the first longitudinal slot defining a first pair of opposing portions biased toward one another.

In an embodiment, the first longitudinal slot includes a proximal portion configured to receive the cam when the arms are in the tissue receiving configuration and a distal portion extending between the distal opening and the proximal portion, the distal portion having a cross-sectional area smaller than a cross-sectional area of the cam.

In an embodiment, the coupling mechanism includes a hook extending distally from an outer surface of the distal portion and configured to be removably received within a hook receiving space of the proximal part, the hook receiving space being positioned distally of the proximal portion of the first longitudinal slot.

In an embodiment, first longitudinal slot proximal portion includes a distal tapered portion that tapers distally to the slot distal portion so that when the cam abuts the distal tapered portion, a proximal force on the proximal portion causes the first opposed portions to spread to permit the cam and the hook to be passed distally out of the first longitudinal slot to disengage the proximal part from the capsule and the distal part.

In an embodiment, the distal part includes a second longitudinal slot extending from a proximal opening at a proximal end of the distal part to a slot distal end, the second longitudinal slot defining a pair of opposed portions biased toward one another, the opposed being spreadable to permit the cam to be passed distally into the second longitudinal slot to lock the distal part to the capsule in the tissue clipping configuration.

The present disclosure also relates to a method for treating tissue. The method includes inserting a distal portion of a clipping device to a target area within a living body, the distal portion including: a capsule extending longitudinally from a proximal end to a distal end and including a channel extending therethrough, the capsule including a cam extending in a direction perpendicular to a longitudinal axis of the capsule from a first wall of the capsule to an opposing wall thereof and clip arms extending from a proximal end to a distal end and configured to be received within the channel of the capsule to be moved between a tissue receiving configuration, in which distal ends of the clip arms are separated from one another, and a tissue clipping configuration, in which distal ends of the clip arms are moved toward one another, the clip arms including a proximal portion and a distal portion coupled to one another via a coupling mechanism, the proximal portion configured to release from the distal portion so that the distal portion remains within the body in the tissue clipping configuration while the proximal portion is removed from the body, positioning the clip arms in contact with a target tissue and clipping the target portion of tissue by positioning the target portion of tissue between the clip arms in the open configuration and drawing the clip arms toward the closed configuration to grip the target portion of tissue.

BRIEF DESCRIPTION

FIG. 1 shows longitudinal, partially-transparent, top view of a clipping device according to an exemplary embodiment of the present disclosure;

FIG. 2 shows an enlarged side view of a proximal portion and a distal portion of a clip arm of the clipping device of FIG. 1;

FIG. 3 shows an enlarged perspective view of a portion of the clipping device of FIG. 1;

FIG. 4 shows an enlarged, partially-transparent view of a portion of the clipping device of FIG. 1;

FIG. 5 shows a partially-transparent top view of the clipping device of FIG. 1 in a clipping configuration;

FIG. 6 shows an enlarged, partially-transparent view of a portion of the clipping device of FIG. 1;

FIG. 7 shows an enlarged, partially-transparent view of a portion of the clipping device of FIG. 1; and FIG. 8 shows a partially-transparent top view of the clipping device of FIG. 1 in a deployed configuration.

DETAILED DESCRIPTION

The present disclosure may be further understood with reference to the following description and the appended drawings, wherein like elements are referred to with the same reference numerals. The present disclosure relates to an endoscopic clipping device for treating tissue perforations, defects and/or bleeds. Exemplary embodiments of the present disclosure describe a hemostatic clip with a two-part arm design. In particular, the arms include proximal and distal portions with the proximal portions disengaging from the distal portions when the clip is deployed, reducing the size of the clip that is left within the body. Current embodiments also include a smaller capsule design for holding the distal portions in the clipped configuration. It should be noted that the terms "proximal" and "distal," as used herein, are intended to refer to toward (proximal) and away from (distal) a user of the device.

As shown in FIG. 1, a clip device 100 according to an exemplary embodiment of the present disclosure comprises a distal portion 102 insertable into a living body through, for example, a working channel of an endoscope to a target tissue to be treated. The device 100 is sufficiently flexible to permit it to traverse a tortuous path through the body—e.g., passing through the working channel of an endoscope inserted through a natural body lumen accessed via a natural bodily orifice. The distal portion 102 includes first and second clip arms 104 slidably received within a longitudinal channel 106 of a capsule 108. The clip arms 104 can be moved between an open configuration, in which distal ends 110 of the clip arms 104 are separated from one another to receive target tissue therebetween, and a closed configuration, in which the distal ends 110 of the clip arms 104 are moved toward one another to grip the target tissue therebetween. The distal portion 102 is releasably coupled to a proximal portion 112 of the device 100, which includes a delivery system, including a control member 114 and a connection member 124, and a handle (not shown) that remains outside the body accessible to a user as the distal portion 102 is deployed. The clip arms 104 are movable between the open and closed configurations via the control member 114 extending into the capsule 108. A proximal end of the control member 114 is connected to an actuator on the handle. In this embodiment, a distal end 116 of the control member is coupled to the proximal ends 118 of the clip arms 104 via the connection member 124 such as, for example, core member shaped so that, when the proximal portions 120 of the arms 104 are bent over the surface of the connection member 124, the bowing of the arms 104 generates a bias toward the open, tissue receiving configuration.

As further shown in FIG. 1, the device 100 includes clip arms 104 each of which, according to an exemplary embodiment of the present disclosure, extends from a proximal end 118 to a distal end 110. As those skilled in the art will understand, the clip arms 104 of this embodiment are biased toward an open tissue receiving configuration so that, when moved distally out of the capsule 108, they spring to the open, tissue receiving configuration. However, those skilled in the art will understand that any number of other mechanisms may be employed to open the clips such as geared mechanisms, camming connections, additional biasing members, etc. In the tissue receiving configuration, the distal ends 110 of the clip arms 104 are spread apart from one another to create a space in which tissue may be received. However, as would be understood by those skilled in the art, the device 100 may include a separate member urging the arms 104 away from one another in addition to, or as an alternative, to the bias. When the clip arms 104 are drawn into the capsule 108, the capsule 108 constrains the clip arms 104, drawing the distal ends 118 thereof together and holding them in the tissue clipping configuration so that they grip any tissue caught therebetween. In this embodiment, the proximal ends 118 of the clip arms 104 are coupled to the connection member 124. In an exemplary embodiment, the distal ends 118 of the clip arms 104 are integrally formed with the connection member 124. However, those skilled in the art will understand that any of the various known mechanisms for releasably coupling a clip assembly (e.g., a capsule including clip arms) to an insertion device may be employed without deviating from the scope of the invention. The clip arms 104 may include optional gripping features configured to facilitate the gripping of tissue therebetween. For example, the distal ends 110 of the clip arms 104 may include tips extending laterally inward toward one another and/or teeth, protrusion, spikes or other structures configured to grip tissue between the distal ends 110 of the clip arms 104.

Each of the clip arms 104, according to an exemplary embodiment of the present disclosure depicted in FIGS. 1-3, has a proximal portion 120 and a distal portion 122 releasably coupled to each other. Specifically, the proximal portion 120 of each arm 104 extends from the proximal end 118 to a proximal portion distal end 126 while the distal portion 122 extends from a distal portion proximal end 128 to the distal end 110. The proximal and distal portions 120, 122, when coupled together, may have substantially the same form and length of any known clip arm. A distal curved portion 121 of the proximal portion 120 is sized and shaped to fit along the outer surface of a proximal curved portion 123 of the distal portion 122 of the clip arms 104, with the curved portion 121 substantially corresponding to the curved portion 123 of the distal portion 122.

The proximal portion 120 is configured to be connected to a hook 130 of the distal portion 122 via opposed members 144 defining a longitudinal slot 132. The longitudinal slot 132 extends from a distal opening 134 at the distal end 126 of the proximal portion 120 along a longitudinal axis of the proximal portion 120 to a proximal portion 136 of the slot 132 that is sized and shaped to receive a cam 138 of the capsule 108. The slot 132 also includes a hook receiving space 140 positioned distally of the proximal portion 136 sized and shaped to receive the hook 130. A distal portion 142 of the slot 132 extending between the distal opening 134 and the hook receiving space 140 has a cross-sectional area (e.g., diameter) smaller than the cross-sectional area of the hook receiving space 140. The opposed members 144 are spreadable to receive the hook 130 and are biased toward one another so that, once the hook 130 has passed proximally into the hook receiving space 140, the opposed members 144 spring back to lock the hook 144 in the hook receiving space 140, coupling the proximal and distal portions 120, 122 of the clip arms 104 to one another. A medial portion 143 of the slot 132 extending between the hook receiving space 140 and the proximal portion 136 of the slot 132 has a cross-sectional area (e.g., diameter) smaller than the cross-sectional area of the proximal portion of the slot 136. As can be seen in FIG. 2, a distal end 135 of the proximal portion 136 of the slot 132 is tapered toward the medial portion 143 of the slot 132 to guide the cam 138 of the capsule out of the slot 132. The opposed members 144 are spreadable upon proximal movement of the cam 138 through the tapered distal end 135 to release the cam 138 from the slot 132 and the proximal portion 120 of the arms 104, as will be described in further detail below. To allow the cam 138 to move smoothly through the slot 132, the hook receiving space 140 has a length smaller than the diameter of the cam 138.

The distal portion 122, as noted above, includes a hook 130 extending distally from an outer surface of the distal portion 122. The hook 130 is configured to be received within the hook receiving space 140 to couple the proximal end distal portions 120, 122 of the arms 104 to the distal portions 122. The distal portion 122 of each arm 104 also includes a pair of opposed members 148 which define a longitudinal slot 150 extending from a proximal opening 152 at the proximal end 128 of the distal portion 122 along a longitudinal axis of the distal portion 122 to a distal slot portion 154 sized and shaped to receive the cam 138 of the capsule 108. As can be seen in FIG. 2, the proximal opening 152 is tapered from the proximal end 128 to a neck portion 156 of the slot 150 to guide the cam 138 of the capsule into the slot 150. The opposed members 148 define the neck portion 156 of the slot 150 which has a cross-sectional area (e.g., diameter) smaller than a cross-sectional area of the cam 138. The opposed members 148 are spreadable to receive the cam and are biased toward one another so that, once the cam 138 has passed distally into the slot 150, the opposed members 148 spring back to lock the cam 138 into the longitudinal slot 150, locking the distal portion 122 to the capsule 108 in the tissue clipping configuration, as will be described in further detail below.

According to this embodiment, the hook 130 of the distal portion 122 may be inserted into the proximal portion slot 132 via the distal opening 134 of the proximal portion 120. When the hook 130 is pushed distally into the proximal portion 120 with a force greater than a predetermined threshold value, the opposed members 144 of the slot 132 deform to permit the hook 130 to pass therethrough into the hook receiving space 140 of the slot. In other words, opposed members 144 separate from one another by a distance sufficient to permit the hook 130 to move proximally therepast through the distal opening 134 and into the hook receiving space 140. Once the hook 130 has been received within the hook receiving space 140, the distal opening 134 reverts to its original size, locking the hook 130 in the hook receiving space 140. Once the hook 130 has been received within the hook receiving space 140, the hook 130 is prevented from moving distally out of the hook receiving space 140 via a distal wall of the hook receiving space 140.

Turning back to FIG. 1, the capsule 108 extends from a proximal end to a distal end and includes a channel 106 extending longitudinally therethrough. The channel 106 is sized and shaped to slidably receive a portion of the clip arms 104 therein. As described above, the capsule 108 also includes a cam 138 which extends across a medial portion of the channel 106 from a first lateral wall of the capsule 108 to a second opposing lateral wall of the capsule 108, perpendicular to a longitudinal axis of the channel 106. The cam 138 may be substantially cylindrical and, in this embodiment, is sized and shaped to be received within the longitudinal slots 132, 150 of the proximal and distal portions 120, 122 of the clip arms 104. It will be understood by those of skill in the art, however, that the cam 138 may have any cross-sectional shape (i.e., square, triangle, oval) so long as the cam 138 is sized to be received through the opposed members 144, 148 and into the slots 132, 150. The capsule 108 further includes a pair of diametrically opposed windows 160 to allow the opposed members 144 of the proximal portion 120 to pass around the cam 138 during the clip release process, as will be described in further detail below. Because the proximal portions 120 of the clip arms 104 are configured to be disengaged from the distal portions 122 of the clip arms 104 and removed from the body after deployment of the clip 100, the capsule 108 need only be long enough to maintain the distal portions 122 of the clip arms 122 in the clipping configuration. Thus, the capsule 108, in this embodiment, is substantially shorter in length than a standard clip capsule. For example, the present capsule may be approximately 0.19 to 0.22 in length, in comparison to a standard capsule which is typically approximately 0.40 to 0.43 in length.

An initial configuration of the clip 100, prior to insertion into the body, can be seen in FIG. 1. In this configuration, the proximal and distal portions 120, 122 of the clip arms are coupled to one another as described above. Additionally, the proximal portions 120 are positioned within the capsule 108 with the cam 138 extending though the longitudinal slots 132 in a direction perpendicular to the longitudinal axis of the longitudinal slots 132. The proximal ends 118 of the proximal portions 120 extend proximally out of the capsule 108 and are coupled with the connection member 124 and control member 114 of the proximal portion 112 of the device 100.

In use, the clip 100 is inserted through a working channel of an endoscope (or any other insertion device) and inserted into the body (e.g., through a natural body lumen) to a site adjacent to a target portion of tissue to be clipped. The clip 100 is inserted to the target tissue in the insertion configuration to facilitate its passage through the working channel. Upon reaching the site of the target tissue, the clip 100 is advanced out of the distal end of the working channel 106 and the clip arms 104 are extended out of the capsule 108 to move the clip arms 104 to the tissue receiving configuration. Once the target tissue has been received between the clip arms 104, the clip 100 may be moved toward the tissue gripping configuration so that the target tissue is gripped between distal ends 110 thereof. The clip arms 104 are moved toward the tissue gripping configuration by drawing the control member 114 proximally with respect to the capsule 108. Once the clip 100 is in the tissue gripping configuration, the control member 114 may be drawn further proximally to lock the clip arms 104 with respect to the capsule 108. Specifically, as the control member 114 is drawn proximally, the proximal and distal portions 120, 122 of the clip arms 104 are drawn proximally and the cam is moved distally through the longitudinal slot 132 of the proximal portion 120 until it abuts the opposed members 148 of the distal portion 122 of the clip arms 104, as shown in FIGS. 4-5. As the control member is drawn further proximally, the tapered ends of the opposed members 148 allow the cam to move through the proximal opening 152 of the distal portion 122 and into the longitudinal slot 150. Once the cam 138 has passed distally into the slot 150, the opposed members 148 spring back to lock the cam into the longitudinal slot 150, locking the distal portion 122 to the capsule 108 in the tissue clipping configuration, shown in FIG. 5.

To deploy the clip 100, the control member 114 is drawn further proximally until the cam 138 abuts the distal tapered end 135 of the longitudinal slot proximal portion 136, as can be seen in FIG. 6. The tapered distal end 135 of the slot 132 allows the proximal portion 120 to move further proximally, spreading the opposed members 144 of the proximal portion 120 away from one another until the hook 130 is released from the hook receiving space 140, as shown in FIG. 7. As the opposed members 144 are spread apart, the windows 160 in the capsule 108 provide the space required for the opposed members 144 to move around the cam 138. Thus, the proximal and distal portions 120, 122 are disengaged from one another so that the distal portion 122 and the capsule 108 remain in the body while the proximal portion 112 (i.e., connection member 124, control member 114, etc.) with the proximal portion 120 attached are removed from the body, as shown in FIG. 8.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A device for treating tissue, comprising:
an insertion section including a flexible member configured to be inserted to a target site within a body, the insertion section including a connection member; and
a clip including a capsule defining a channel extending therethrough and first and second clip arms, each of the first and second clip arms including a proximal part releasably coupled to a distal part, at least a proximal portion of the distal part of each of the first and second clip arms configured to be slidably received within the channel of the capsule so that the first and second clip arms move proximally and distally relative to the capsule between a tissue receiving configuration, in which distal ends of the distal parts of the first and second clip arms are separated from one another, and a tissue clipping configuration, in which the distal ends of distal parts of the first and second clip arms are moved toward one another, the proximal portion of each of the first and second clip arms being configured to release from the corresponding distal part to lock the distal part of each of the first and second clip arms over a portion of target tissue to be clipped while the proximal parts of the first and second clip arms are removed from the body, wherein the proximal parts of the first and second clip arms are bent over the connection member to bias the first and second clip arms to the tissue receiving configuration.

2. The device of claim 1, wherein the clip further comprises a cam extending into the channel, the cam being configured to lock the distal part of each of the first and second clip arms over the portion of the target tissue to be clipped while the proximal parts of the first and second clip arms are removed from the body.

3. The device of claim 2, wherein the cam is sized and shaped to extend through a first longitudinal slot extending through the proximal parts of each of the first and second clip arms to releasably couple the proximal part of each of the first and second clip arms to the capsule, each of the first longitudinal slots extending from a distal opening at a distal end of the proximal part of the corresponding one of the first and second clip arms along a longitudinal axis of the proximal part of the corresponding one of the first and second clip arms to a slot proximal end, each of the first longitudinal slots defining a first pair of opposing portions biased toward one another.

4. The device of claim 3, wherein each of the first longitudinal slots includes a proximal portion configured to receive the cam when the first and second clip arms are in the tissue receiving configuration and a distal portion extending between the distal opening and the proximal portion, the distal portion of each of the first longitudinal slots having a cross-sectional area smaller than a cross-sectional area of the cam.

5. The device of claim 4, further comprising:
a first coupling mechanism coupling the proximal part of the first clip arm to the distal part of the first clip arm, wherein the first coupling mechanism includes a hook extending distally from an outer surface of a distal portion of the distal part of the first clip arm and configured to be removably received within a hook receiving space of the proximal part of the first clip arm, the hook receiving space being positioned distally of the proximal portion of the first longitudinal slot of the proximal part of the first clip arm.

6. The device of claim 5, wherein the proximal portion of the first longitudinal slot of the first clip arm includes a distal tapered portion that tapers distally to the distal portion so that when the cam abuts the distal tapered portion, a proximal force exerted on the proximal part of the first clip arm causes the first pair of opposing portions of the first longitudinal slot to spread permitting the cam and the hook to pass distally out of the first longitudinal slot of the first clip arm disengaging the proximal part of the first clip arm from the capsule and the distal part of the first clip arm.

7. The device of claim 6, wherein the distal part of the first clip arm includes a second longitudinal slot extending from a slot proximal opening at a proximal end of the distal part of the second clip arm to a slot distal end, the second longitudinal slot defining a second pair of opposed portions biased toward one another, the opposed portions being spreadable to permit the cam to pass distally into the second longitudinal slot to lock the distal part of the first clip arm to the capsule in the tissue clipping configuration.

8. The device of claim 7, wherein the second longitudinal slot includes a proximal neck portion and a distal portion, the proximal neck portion having a cross-sectional area that is smaller than a cross-sectional area of the cam.

9. The device of claim 8, wherein the slot proximal opening tapers from the proximal end of the distal part of the first clip arm to the proximal neck portion to guide the cam into the second longitudinal slot.

10. A system for clipping tissue, comprising:
an insertion member including a lumen extending therethrough;
a control member extending through the lumen of the insertion member, a distal end of the control member coupling to a connection member and a proximal end of the control member being coupled to an actuator that remains accessible to a user so that actuation of the actuator moves the control member and the connection member distally and proximally relative to the insertion member; and
a clip coupled to the connection member, the clip including:
a capsule including a proximal end releasably coupled to a distal end of the insertion member, the capsule defining a channel extending therethrough; and
first and second clip arms each including a proximal part releasably coupled to a distal part, at least a proximal portion of the distal part of each of the first and second clip arms configured to be slidably received within the channel of the capsule so that, as actuation of the actuator moves the control member and the connection member to move proximally and distally relative to the insertion member, the first and second clip arms move proximally and distally relative to the capsule between a tissue receiving configuration, in which distal ends of the distal parts of the first and second clip arms are separated from one another, and a tissue clipping configuration, in which the distal ends of the distal parts of the first and second clip arms are moved toward one another, the proximal portion of each of the first and second clip arms being configured to release from the corresponding distal part, the proximal parts of the first and second clip arms being bent over the connection member to bias the first and second clip arms toward the tissue receiving configuration.

11. The system of claim 10, further comprising a cam extending into the channel configured to lock the distal part of each of the first and second clip arms over a portion of target tissue to be clipped while the proximal parts of the first and second clip arms are removed from a body.

12. The system of claim 11, wherein the cam is sized and shaped to extend through a first longitudinal slot extending through the proximal parts of each of the first and second clip arms to releasably couple the proximal part of each of the first and second clip arms to the capsule, each of the first longitudinal slots extending from a distal opening at a distal end of the proximal part of the corresponding one of the first and second clip arms along a longitudinal axis of the proximal part of the corresponding one of the first and second clip arms to a slot proximal end, each of the first longitudinal slots defining a first pair of opposing portions biased toward one another.

13. The system of claim 12, wherein each of the first longitudinal slots includes a proximal portion configured to receive the cam when the first and second clip arms are in the tissue receiving configuration and a distal portion extending between the distal opening and the proximal portion, the distal portion of each of the first longitudinal slots having a cross-sectional area smaller than a cross-sectional area of the cam.

14. The system of claim 13, further comprising:
a first coupling mechanism coupling the proximal part of the first clip arm to the distal part of the first clip arm, wherein the first coupling mechanism includes a hook extending distally from an outer surface of the distal portion of the distal part of the first clip arm and configured to be removably received within a hook receiving space of the proximal part of the first clip arm, the hook receiving space being positioned distally of the proximal portion of the first longitudinal slot of the proximal part of the first clip arm.

15. The system of claim 14, wherein the proximal portion of the first longitudinal slot of the first clip arm includes a distal tapered portion that tapers distally to the distal portion so that when the cam abuts the distal tapered portion, a proximal force exerted on the proximal part of the first clip arm causes the first opposing portions to spread permitting the cam and the hook to pass distally out of the first longitudinal slot of the first clip arm disengaging the proximal part of the first clip arm from the capsule and the distal part of the first clip arm.

16. The system of claim 14, wherein the distal part of the first clip arm includes a second longitudinal slot extending from a slot proximal opening at a proximal end of the distal part of the second clip arm to a slot distal end, the second longitudinal slot defining a second pair of opposed portions biased toward one another, the opposed portions being spreadable to permit the cam to pass distally into the second longitudinal slot to lock the distal part of the first clip arm to the capsule in the tissue clipping configuration.

\* \* \* \* \*